United States Patent [19]

Stefanchik et al.

[11] Patent Number: 6,071,289
[45] Date of Patent: Jun. 6, 2000

[54] SURGICAL DEVICE FOR SUTURING TISSUE

[75] Inventors: David Stefanchik, Mason, Ohio; John E. Burbank, III, Ridgefield, Conn.; Inbae Yoon, Phoenix, Md.; Ron J. Brinkerhoff, New Richmond, Ohio

[73] Assignee: Ethicon Endo-Surgery, Inc., Cincinnati, Ohio

[21] Appl. No.: 09/270,483

[22] Filed: Mar. 15, 1999

[51] Int. Cl.$^7$ .................................................. A61B 17/04
[52] U.S. Cl. .......................... 606/147; 606/144; 606/148
[58] Field of Search .................................. 606/144, 139, 606/147, 148, 205, 206

[56] References Cited

U.S. PATENT DOCUMENTS

| | | |
|---|---|---|
| 2,363,334 | 11/1944 | Jones . |
| 5,100,421 | 3/1992 | Christoudias ............................ 606/147 |
| 5,152,769 | 10/1992 | Baber ....................................... 606/145 |
| 5,171,257 | 12/1992 | Ferzli ....................................... 606/205 |
| 5,224,948 | 7/1993 | Abe et al. ................................ 606/147 |
| 5,261,917 | 11/1993 | Hasson et al. ........................... 606/139 |
| 5,300,082 | 4/1994 | Sharpe et al. ............................ 606/147 |
| 5,389,103 | 2/1995 | Melzer et al. ............................ 606/144 |
| 5,397,325 | 3/1995 | Della Badia et al. ................... 606/144 |
| 5,437,681 | 8/1995 | Meade ...................................... 606/145 |
| 5,454,823 | 10/1995 | Richardson et al. .................... 606/148 |
| 5,540,705 | 7/1996 | Meade ...................................... 606/145 |
| 5,674,230 | 10/1997 | Tovey ....................................... 606/139 |
| 5,735,862 | 4/1998 | Jennings .................................. 606/147 |
| 5,759,188 | 6/1998 | Yoon ........................................ 606/147 |
| 5,897,563 | 4/1999 | Yoon et al. .............................. 606/147 |
| 5,954,731 | 9/1999 | Yoon ........................................ 606/144 |
| 5,954,733 | 9/1999 | Yoon ........................................ 606/147 |
| 5,957,937 | 9/1999 | Yoon ........................................ 606/147 |
| 5,984,932 | 11/1999 | Yoon ........................................ 606/147 |
| 5,993,466 | 11/1999 | Yoon ........................................ 606/147 |
| 5,993,467 | 11/1999 | Yoon ........................................ 606/147 |

FOREIGN PATENT DOCUMENTS

| | | |
|---|---|---|
| 0 482881A1 | 4/1992 | European Pat. Off. ........ A61B 17/04 |
| 0705569 | 10/1996 | European Pat. Off. ........ A61B 17/04 |
| 337579 | 12/1903 | France . |
| 94 04 458 | 8/1995 | Germany . |
| 2260704A | 9/1991 | United Kingdom ........... A61B 17/04 |

*Primary Examiner*—Gary Jackson
*Attorney, Agent, or Firm*—Dean L. Garner

[57] ABSTRACT

A surgical device is described for assisting a surgeon in suturing bodily tissue using a curved, surgical needle with a suture filament attached. The surgical device comprises a handle, an elongated shaft having a proximal end, a distal end, and a longitudinal axis extending in between. The device further comprises a stationary arm having a first holder fixedly attached to and extending from the distal end of the shaft, and used for operationally engaging with the needle. The device also has a movable arm having a second holder extending from the distal end of the shaft and rotatable around the longitudinal axis of the device. The movable arm also is operationally engageable with the needle. An actuator is provided for cooperatively actuating the first and second holders, so as to be able to pass a needle along a circular path transverse to the longitudinal axis of the device through the tissue, and thus place the suture filament into the tissue.

19 Claims, 13 Drawing Sheets

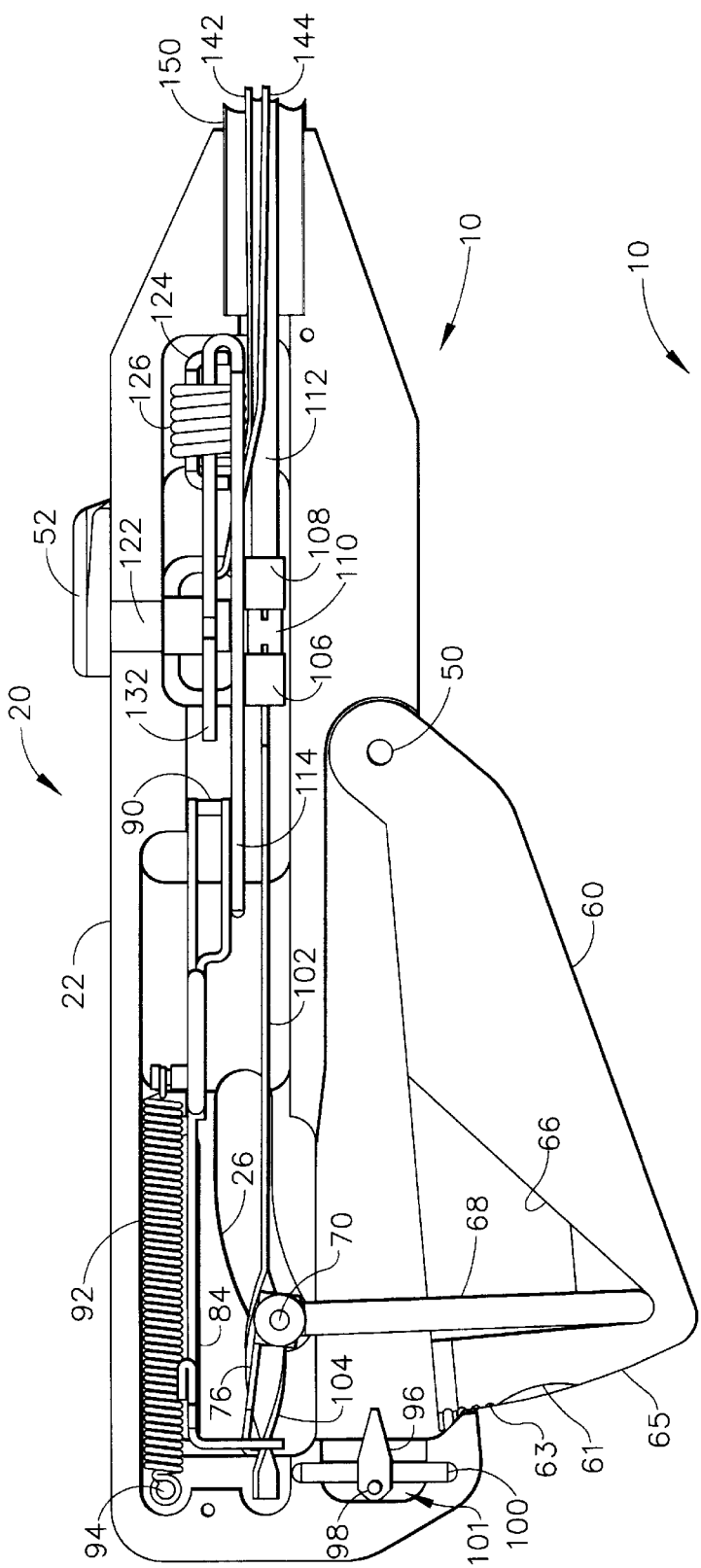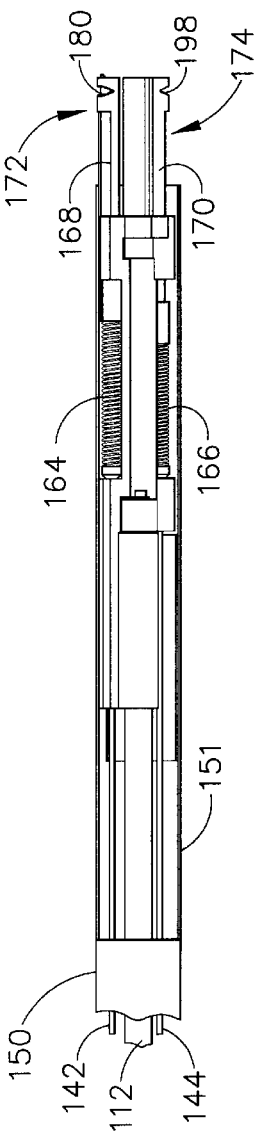
FIG. 4
FIG. 5

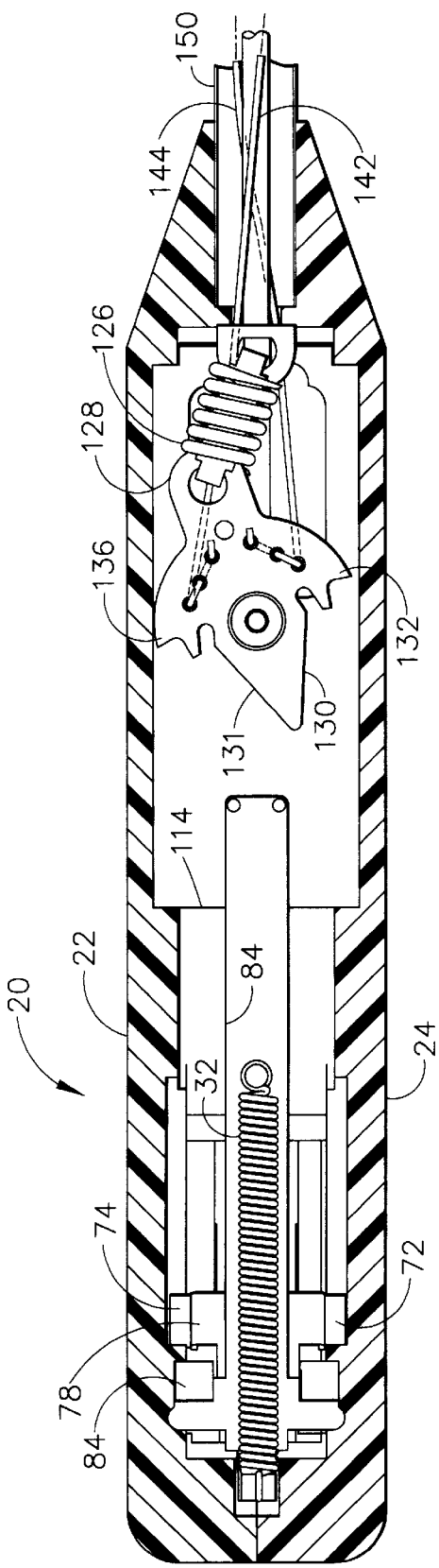
FIG. 9
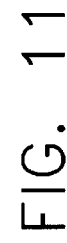
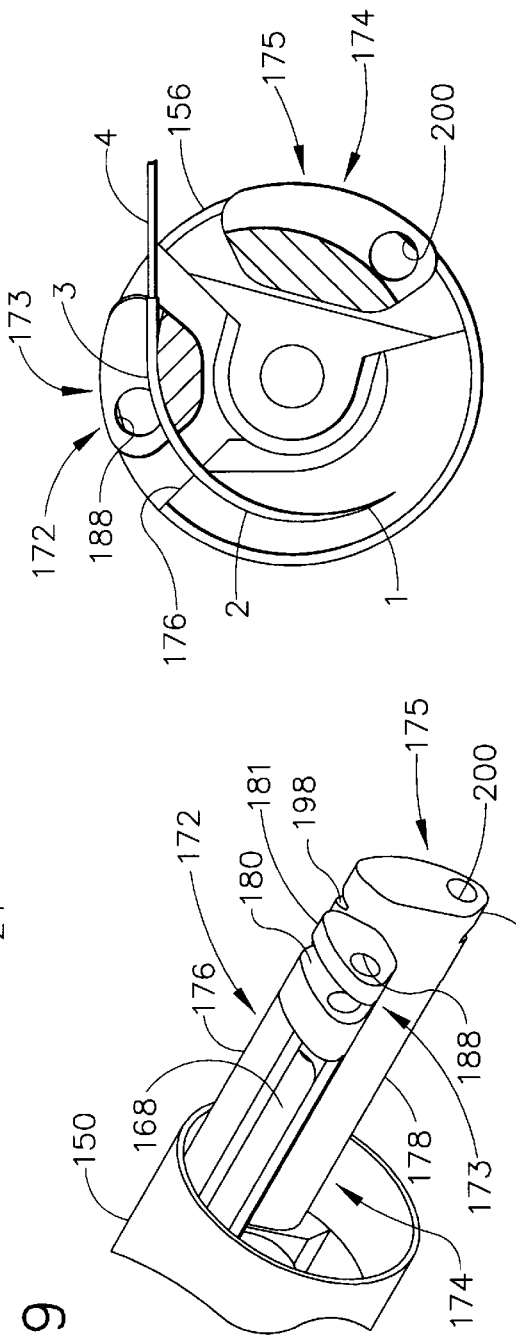
FIG. 11
FIG. 10

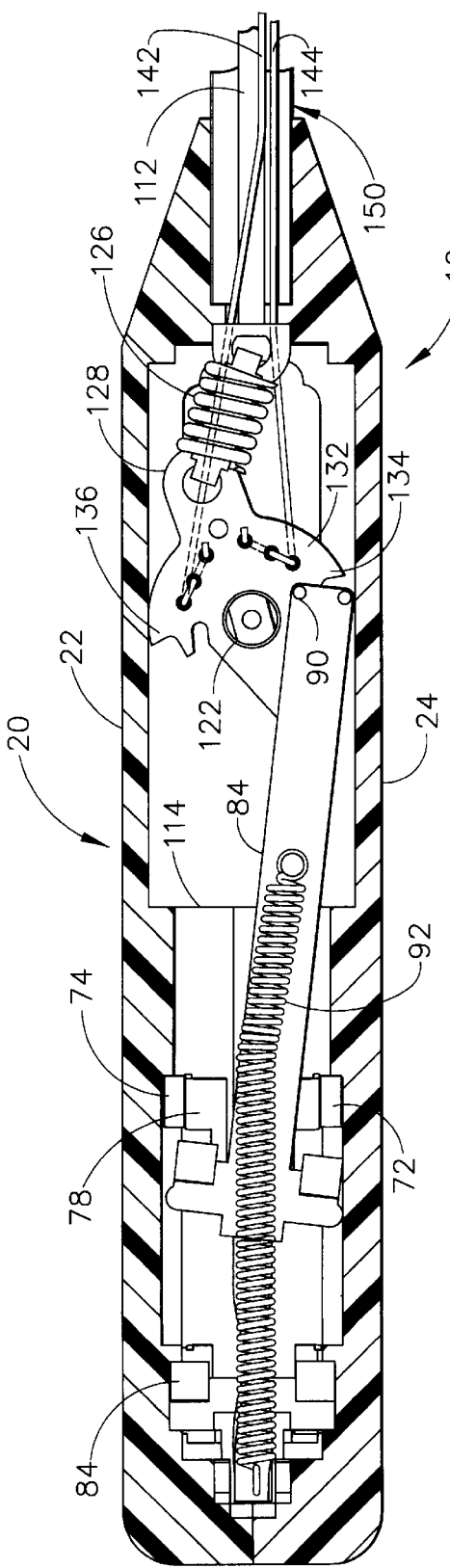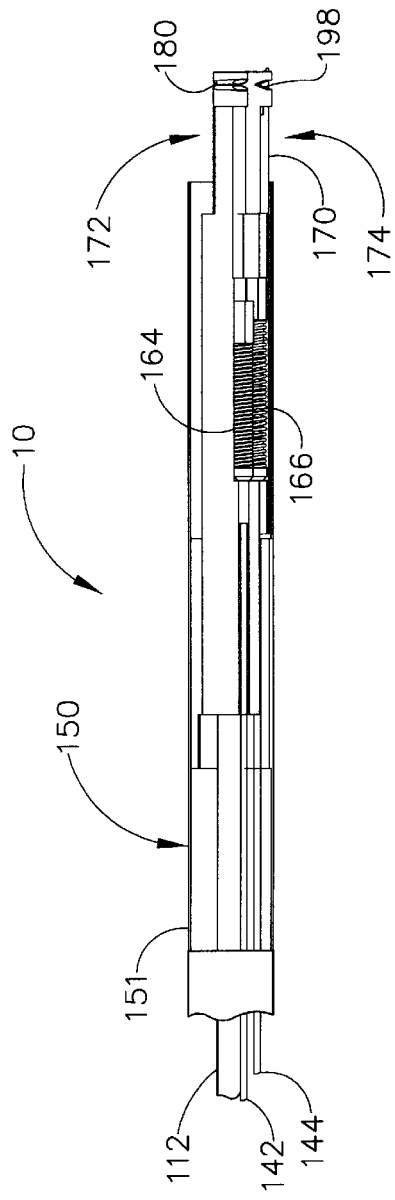

SURGICAL DEVICE FOR SUTURING TISSUE

FIELD OF THE INVENTION

The present invention relates to the field of medicine and more particularly to surgery. More specifically, the present invention relates to surgical devices and methods for suturing bodily tissues both for open surgical procedures and for endoscopic surgical procedures. The present invention especially relates to surgical devices and methods for joining hollow organs, e.g. the anastomosis of the small or large intestines, and blood vessels, for joining them together in end-to-end, end-to-side, or side-to-side fashion.

BACKGROUND OF THE INVENTION

It is common surgical practice to use bypass grafts to help reestablish coronary artery circulation when a portion of the coronary artery is stenosed. Such a procedure is typically referred to as a Coronary Artery Bypass Graft (CABG) procedure. Typically the graft vessel used in bypassing the stenosed portion of the coronary artery comprises one or more segments of the patient's saphenous vein which is taken from his leg. The saphenous vein is dissected free from the leg, its side branches tied off or ligated, and the vein removed. The vein graft is then washed free of blood, and cut into portions of suitable length. Each portion is then passed to the surgeon who trims the ends of the graft before anastomosing the graft to the aorta and the coronary artery. Other graft vessels such as the radial artery in the arm can also be used. In addition, it is common practice today for the surgeon to redirect one of the internal mammary arteries (IMA) in the chest to the stenosed portion of the left anterior descending (LAD) artery on the heart. The end of the IMA near the patient's diaphragm is transected, the artery is mobilized by dissection and ligation of side branches, and then the end is joined to the LAD, just distal to the blockage. For multiple bypass surgery, a combination of the redirection of the IMA and the grafting of vessels to the diseased coronary arteries is often used.

Some surgeons choose to complete all the proximal anastomoses to the aorta before commencing the distal anastomoses to the coronary arteries. In contrast, others choose to complete the distal anastomoses first. Regardless of the order, when undertaking the distal anastomoses to the coronary artery, it is important that the vessel graft be held steady and adjacent the coronary artery, with a minimum of vascular trauma and a minimum of visual and surgical obstruction by instruments in the narrow operative field.

The speed of performing such anastomoses can become extremely critical as well. Often the coronary artery is occluded during the procedure so that the anastomoses can be performed more easily. It is very important to reconnect the supply of blood to artery as soon as possible in order to minimize or prevent damage to the patient. Blood vessels are now normally anastomosed end-to-end or end-to-side by suturing techniques. Conventionally, to suture two vessels together, a surgeon passes the pointed tip of a curved suturing needle, having a suture attached to the blunt end, through the coronary artery wall from inside the lumen. The needle is then passed through the graft vessel wall from the outside. Then, the surgeon grasps the tip of the needle which has been forced through the tissues with a needle holder and pulls the needle through the tissues, the suture following the curved path of the needle. Usually a knot or button is present at the trailing end of the suture to anchor the first stitch. After the surgeon has pulled the suture entirely through the tissues to tension the first stitch, he or she then forces the tip of the needle through the coronary artery again, at a location spaced from the first stitch, until the needle again goes through the coronary artery and back out through the graft vessel. Again, he grasps the tip of the needle which has been forced through the tissues, applies tension to the needle pulls the entire suture through the tissues to complete the second stitch. This process is repeated again and again, with the surgeon tensioning the suture after each stitch to draw the tissues together thereby creating a running or continuous stitch composed of individual thread loops, which extends around the graft vessel.

In a CABG, access to the heart is gained through a median sternotomy. Less invasive procedures are being widely adopted in order to reduce the recovery time and the associated post-operative pain of the patient. One procedure, known as a MIDCAB (minimally invasive direct coronary artery bypass) is performed through an intercostal (between the ribs) incision or thoracotomy. Endoscopic procedures for other parts of the body and involving the suturing of tissue are well known in the surgical art.

Needless to say, such suturing techniques are a tedious and time consuming task, especially when access to the surgical site is limited. Suture anastomoses procedures generally take the skilled surgeon several minutes to complete for each anastomosis. An example of a device which was designed to help a physician in performing suturing can be found in U.S. Pat. Nos. 5,437,681 issued to Meade, et al. on Aug. 1, 1995 and 5,540,705 issued to Meade, et al. on Jul. 30, 1996. However, there are a number of disadvantages to the device disclosed in those references. In those devices it is the device itself which drives the needle through the tissue. Many physicians do not like this design because they like to have more control of needle placement and feel the resistance of the needle passing through the tissue when doing the procedure. Surgeons want the speed and efficacy offered by the new devices, but surgeons also want to maintain the benefits of the traditional suturing techniques.

It is also important to surgeons to be able to use various types of surgical needles which are commercially available today. This is because different surgical procedures require different needles (and suture filaments) and because of differences in surgical technique. Needles may be semi-circularly shaped (having a single center of curvature) of different radii. Others are arcuate, and may have multiple centers of curvature. It is desired that a needle-holding device overcome the shortcomings of the prior art already cited, yet also be able to accommodate these various needles.

Sometimes it is necessary or unavoidable for the surgeon to apply a side force to the needle as it is being passed through the tissue. This may happen, for example, if the surgeon has placed the needle into the tissue, and then raises or twists the needle holder to augment the position of the tissue captured. The side force could result in the deflection of the needle while held in the end effectors of the needle holder. This is not so much a problem if a second needle holder is used to clamp onto the pointed end of the needle and pull it from the tissue. A single surgical device having both the ability to place the needle into tissue and to pull the needle from the opposite side of the tissue so as to make a stitch with one device, yet never letting loose of the needle, must allow for the needle deflection sometimes encountered. All of this must be done while managing the trailing suture filament attached to the needle so that the filament is not inadvertently damaged or tangled.

Typically the step of the suturing technique that requires the most time and care is the accurate placement and penetration of the needle into the tissue. Once the needle is penetrated into the tissue so that the needle tip exits the tissue, the surgeon may quickly pull the needle and trailing suture filament through the tissue. The placement and penetration of the needle into the tissue, therefore, is preferably controlled by the surgeon for some surgical procedures, rather than automated as with some of the prior art devices. Furthermore, it is important for the surgeon to sense tactilely the force of the needle penetrating into tissue in order to understand the type of tissue being penetrated or to know if obstructions are in the way of the needle. This control and tactile feedback may be provided by using a surgical instrument to hold the needle near the attachment to the suture filament, placing the tip of the needle into the tissue, and then rotating the instrument about its longitudinal axis in order to penetrate the tip of the needle through the tissue. Rotation of the instrument is accomplished by the medial rotation of the surgeon's forearm. (This is referred to in the art as supination for when the palm is turned upward and pronation for when the palm is turned downward.) What is needed, therefore, is a surgical instrument that allows the surgeon to control and have tactile feedback for the step of needle placement and penetration, yet automates the less critical step of pulling the needle and filament through the tissue.

The present invention provides a device and method that overcomes the shortcomings of the prior art and helps the physician to suture bodily tissues easily and quickly with a single instrument. It may be used for many different shapes of surgical needles, not only semi-circular ones. The present invention provides a device that can both place the needle into tissue, and pull the needle from the opposite side of the tissue, without letting go of the needle. It can do so even though a side force may be applied to the needle. The present invention provides a stationary arm for holding the needle so that the surgeon may retain control and tactile feedback of the step of placing and penetrating the needle into the tissue. The present invention provides a movable arm to automate the pulling of the needle and filament through the tissue. The present invention provides for management of the suture filament as the needle is manipulated through the tissue. It may be used in open surgeries as well as in the less invasive and endoscopic procedures. All of these attributes make the present invention especially useful for performing and easy and quick vascular anastomoses such as for a CABG procedure.

SUMMARY OF THE INVENTION

In accordance with the present invention there is provided a device for assisting a physician in suture procedures using a curved needle having a suture attached thereto. The surgical device comprises a handle, an elongated shaft having a distal end, a proximal end, and a longitudinal axis extending therebetween. The device further includes a stationary arm having a first holder fixedly attached to and extending from the distal end of the shaft. The first holder of the stationary arm is for operationally engaging the needle so that the device can be used as a needle holder for placing the needle into the tissue. The device further includes a movable arm having a second holder extending from the distal end of the shaft. The second holder of the movable arm is rotatable around the longitudinal axis of the device, and is also operationally engageable with the needle. The movable arm moves the needle between a first and second position, so that the curved needle follows a circular path around the longitudinal axis of the device. An actuator is provided for cooperatively actuating the first and second holders for placing the suture filament attached to the needle into the tissue.

BRIEF DESCRIPTION OF THE DRAWINGS

FIG. 4 is a side view of the internal components of a handle of the surgical device, for when the handle is in a first configuration;

FIG. 5 is a side view of the internal components of the distal portion of a shaft of the surgical device, correlating with the handle configuration of FIG. 4;

FIG. 9 is a top view of the internal components of the handle of the surgical device, for when the handle is in a second configuration;

FIG. 10 is an isometric view of the distal portion of the shaft of the surgical device, correlating with the second handle configuration of FIG. 9;

FIG. 11 is an sectional end view of the distal portion of the surgical device, showing a needle in a loaded position, correlating with the first handle configuration shown in FIG. 6.

FIG. 14 is a top view of the internal components of the handle of the surgical device, correlating with the third handle configuration of FIG. 12;

FIG. 15 is a top view of the internal components of the distal portion of the shaft, correlating with the third handle configuration of FIG. 12;

The drawings are not to scale.

DETAILED DESCRIPTION OF THE PREFERRED EMBODIMENT

Figure 1:
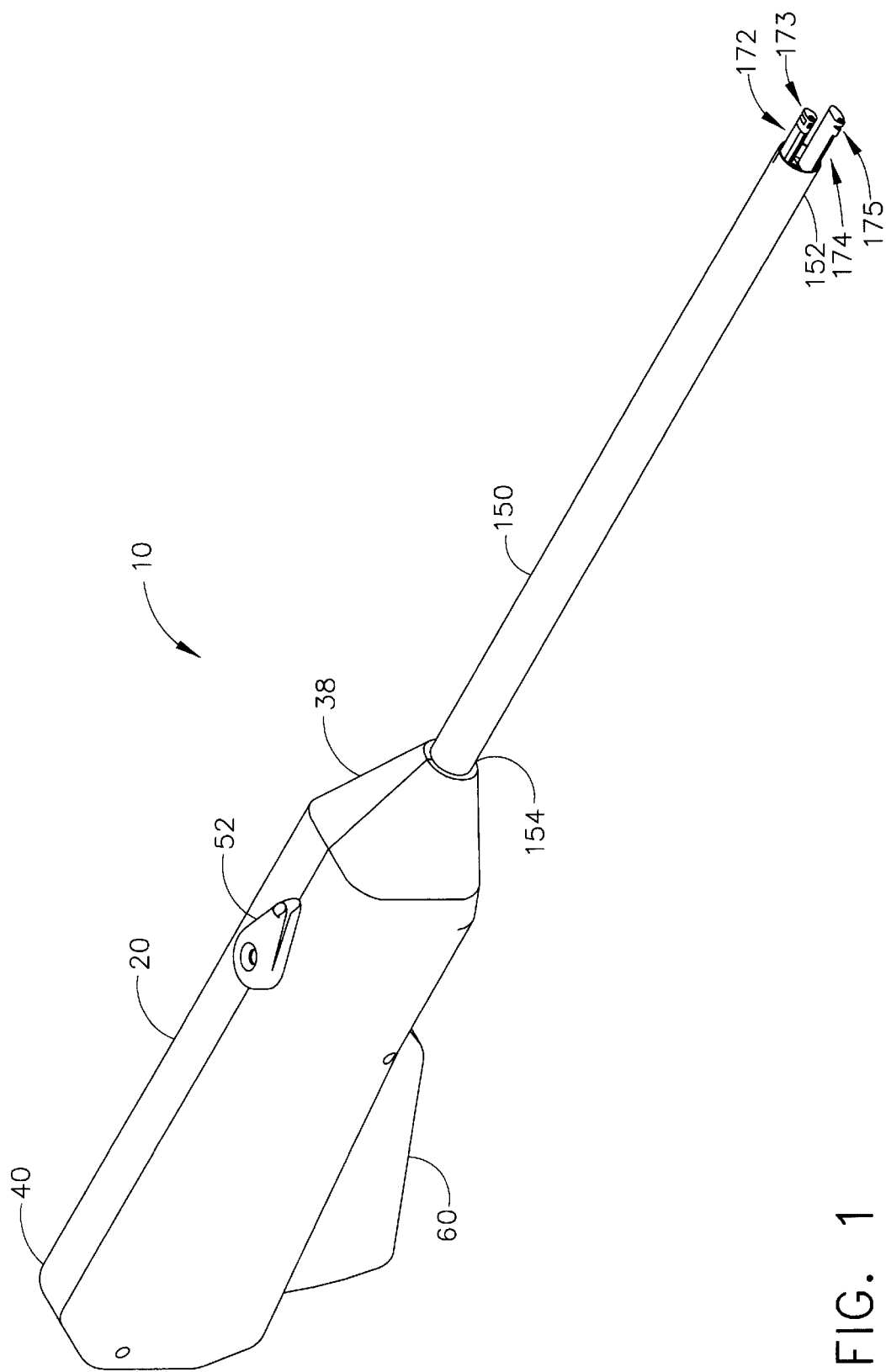
FIG. 1 is an isometric view of the present invention, a surgical device.

FIG. 1 is an isometric view of a preferred embodiment, a surgical device 10, of the present invention. The surgical device 10 generally comprises a handle 20 and an elongated shaft 150 extending from the handle 20. The handle 20 comprises a proximal end 40, a distal end 38, an actuator 60, and a control 52. The shaft 150 has a proximal end 154 and a distal end 152. Extending from the shaft distal end 152 is a stationary arm 172 having a first holder 173. Also extending from the shaft distal end 152 is a movable arm 174 having a second holder 175.

Figure 17:
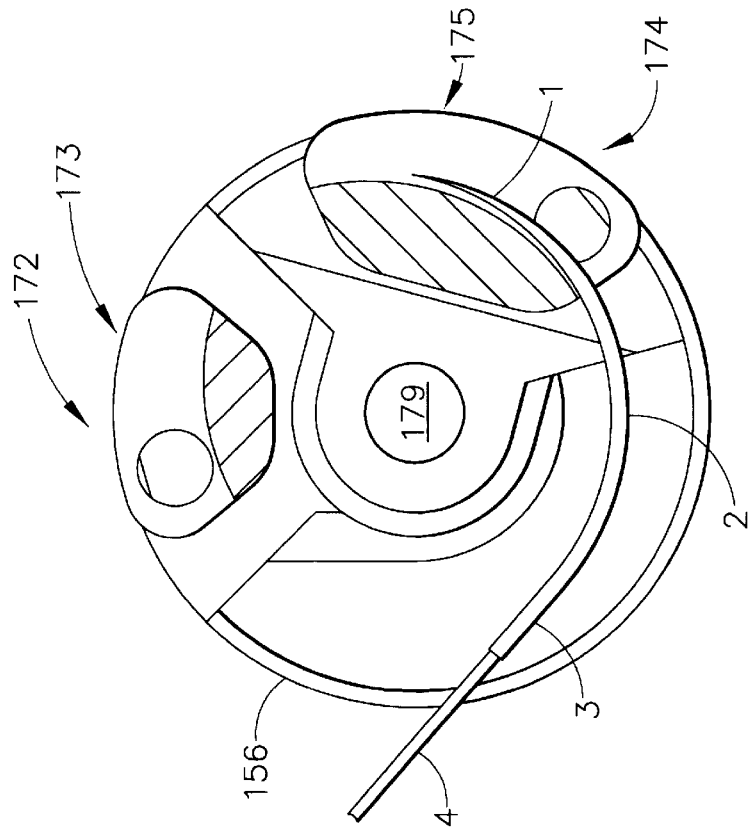
FIG. 17 is a sectional end view of the surgical device for when the needle is being held by both a first holder of a stationary arm and a second holder of a movable arm, the latter of which is at a first position.
Figure 18:
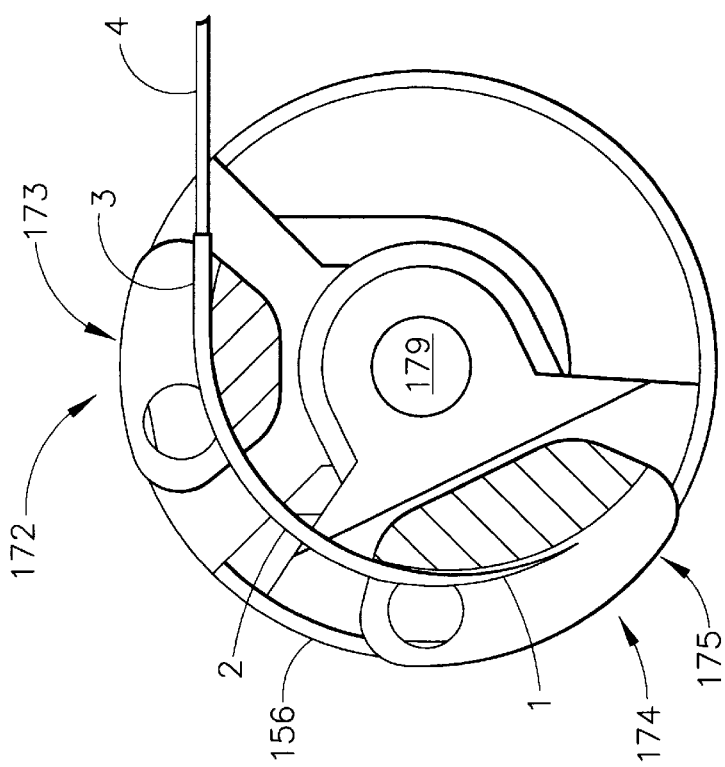
FIG. 18 is a sectional end view of the surgical device for when the needle is held only by the second holder of the movable arm which is at a second position.

Before the components and their structural relationships are described, reference is first made to FIGS. 11, 17 and 18 for a general understanding of the function of the stationary arm 172 and the movable arm 174. For clarity, the tissue has been removed from the views in FIGS. 11, 17, and 18.

FIG. 11 is a sectional end view of the distal end 152 of the shaft 150. A curved needle 2 having a sharp end 1, a blunt end 3, and a suture filament 4 attached, is shown securely held in the first holder 173 of the stationary arm 172. The second holder 175 of the movable arm 174 is shown in a position removed from the stationary arm 172, hereinafter referred to as a second position of the movable arm 174. In FIG. 11, the needle 2 is ready for placement into tissue. The surgeon locates the sharp end 1 of the needle 2 in the tissue and then supinates (turns palm of right hand upward in a clockwise motion) the entire surgical device 10 so that the needle 2 may further penetrate the tissue, until the sharp end 1 exits on the far side of the tissue.

FIG. 17 is the same sectional end view as shown in FIG. 11, but for when the movable arm 174 has rotated about pin 179 to a position hereinafter referred to as a first position of the movable arm 174. The sharp end 1 of the needle 2 is securely held by the movable arm 174. The blunt end 3 of the needle 2 is securely held by the stationary arm 172. Tissue is positioned on the needle 2 and between the movable and stationary arms, 172 and 174 respectively.

FIG. 18 is the same sectional end view as shown in FIGS. 11 and 18, but for when the movable arm 174 has returned to the second position by rotating about the pin 179. The blunt end 3 of the needle 2 has been released by the stationary arm 172 while the sharp end 1 has been securely held by the movable arm 174. During the rotation of the movable arm 174, the suture filament 4 is automatically passed through the tissue. At this point, the surgeon may carefully withdraw the surgical device 10 from the surgical site, pulling suture filament 4 through the tissue. The surgical device 10 may be prepared for another stitch using the same or a different needle with suture. If using the same needle 2, then another cycle of the actuator 60 will return the needle 2 to the starting position, where it is secured in the stationary arm 172.

Figure 2:
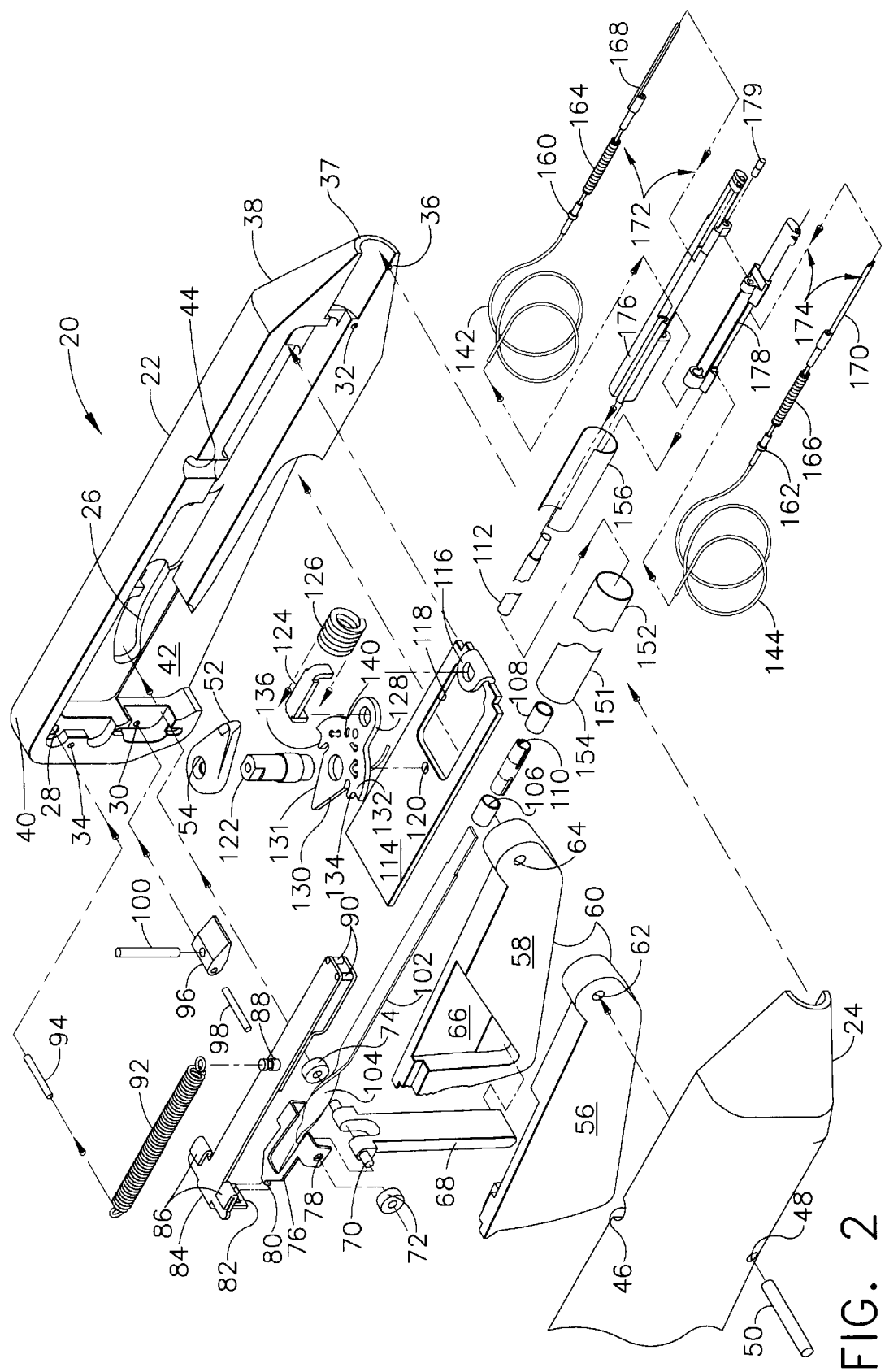
FIG. 2 is an exploded isometric view of the surgical device.
Figure 3:
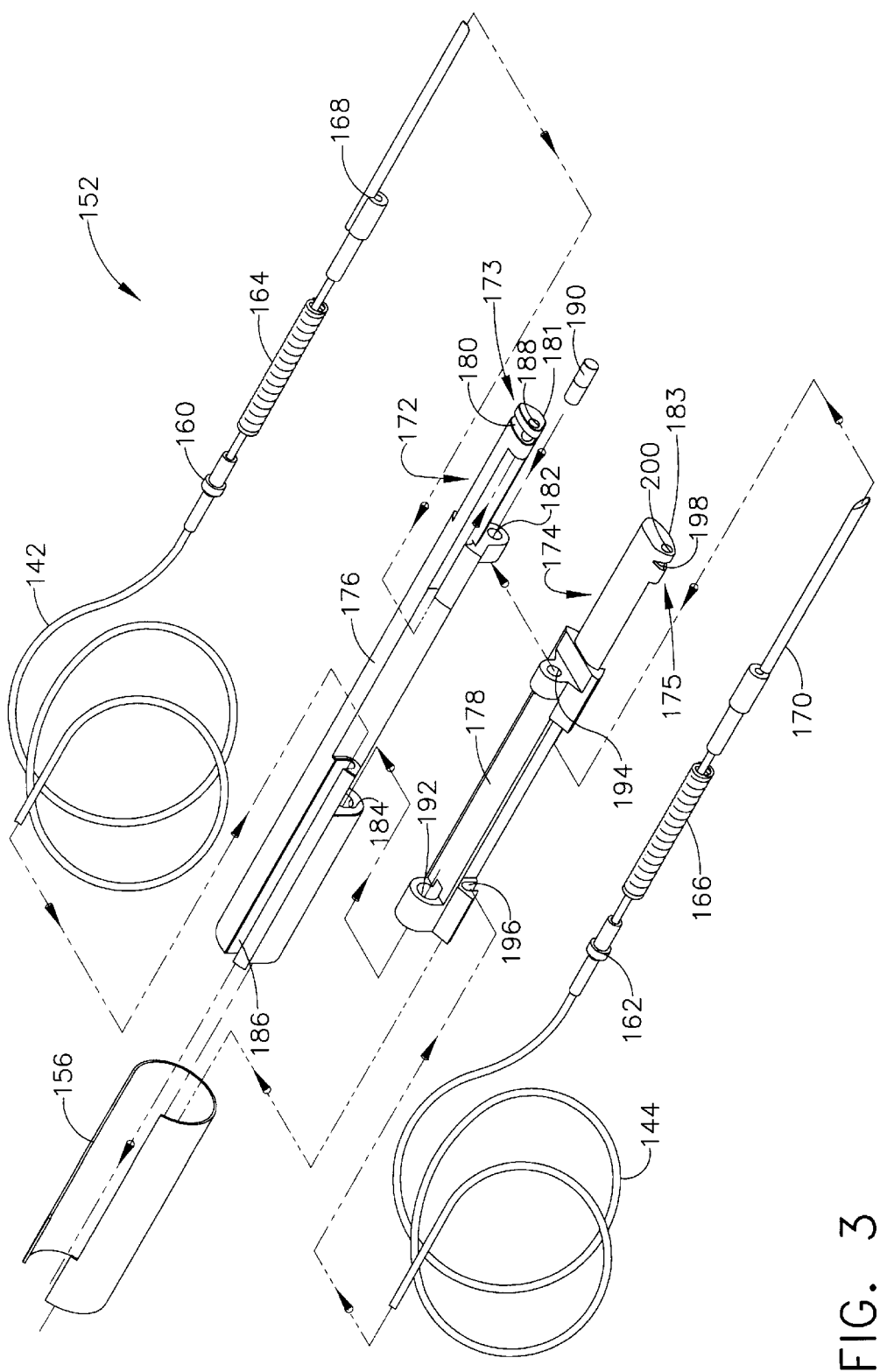
FIG. 3 is an exploded isometric view of the distal portion of the surgical device.
Figure 6:
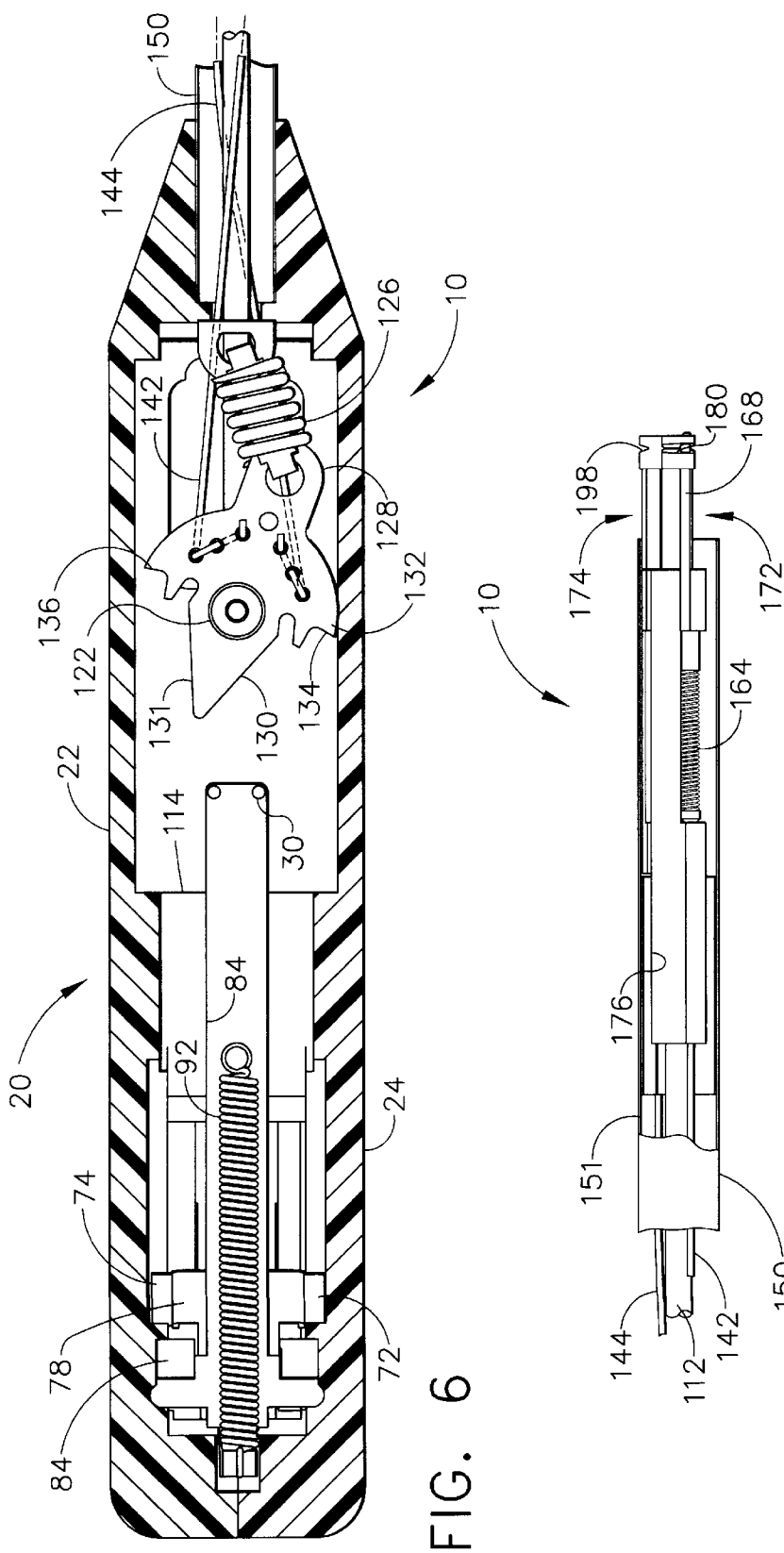
FIG. 6 is a top view of the internal components of the handle of the surgical device, for when the handle is in the first configuration.
Figure 7:
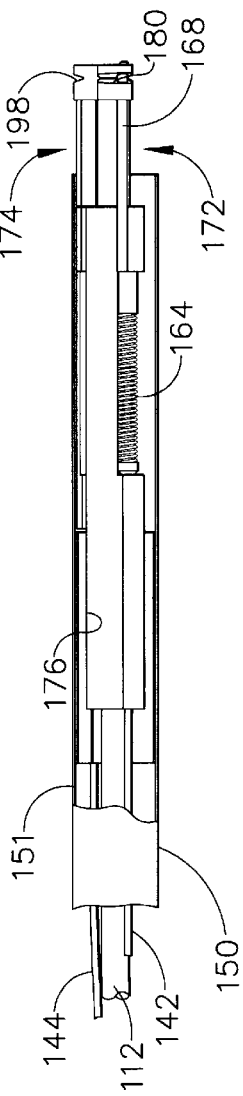
FIG. 7 is a top view of the internal components of the distal portion of the shaft of the surgical device, correlating with the first handle configuration of FIG. 6.
Figure 8:
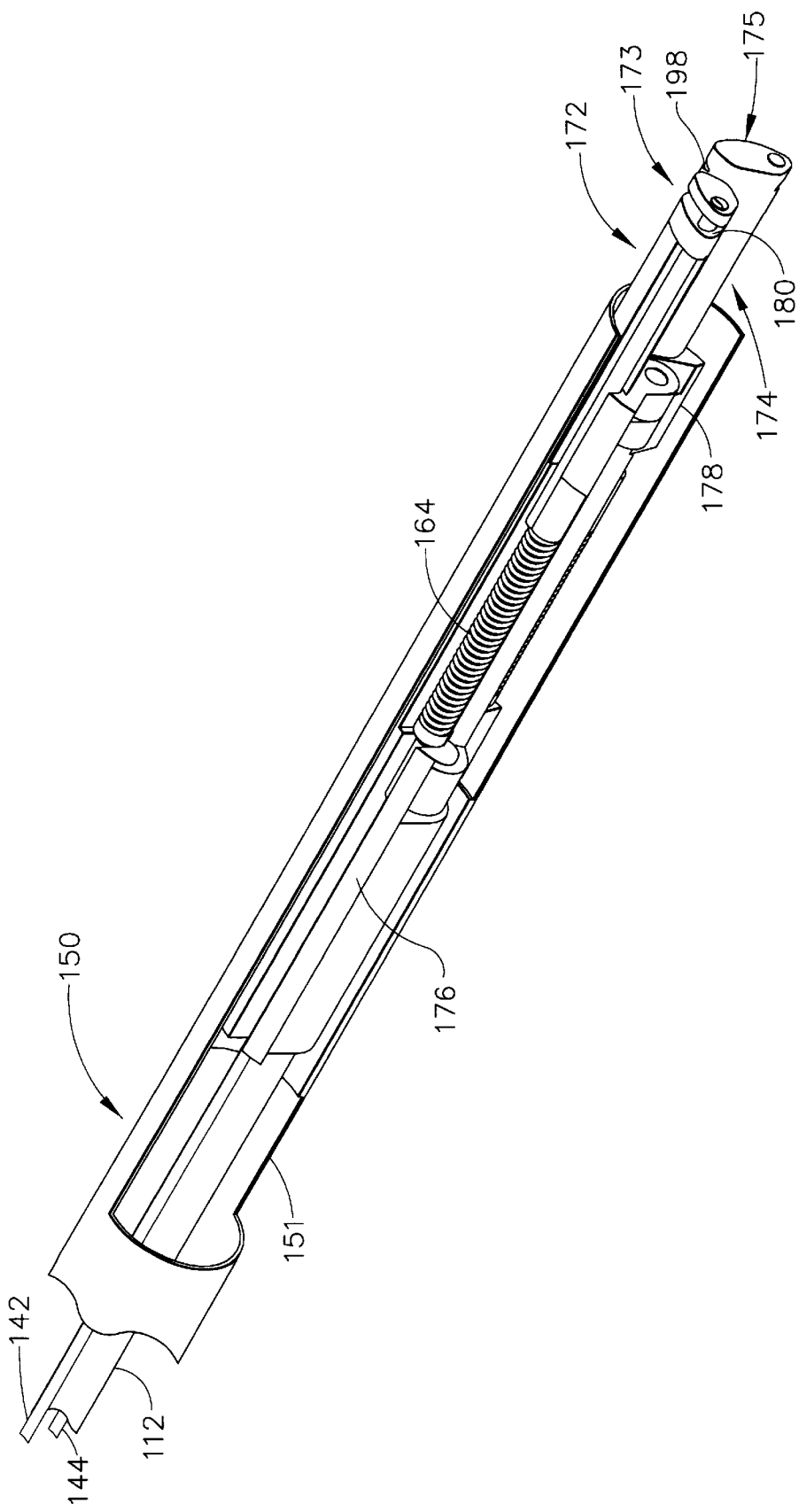
FIG. 8 is an isometric view of the distal portion of the shaft of the surgical device with a portion of the shaft tube cutaway for clarity, correlating with the first handle configuration of FIG. 6.

FIG. 3 is an exploded, isometric view of the distal end 152 of the surgical device 10. The stationary arm 172 comprises a first frame 176, a first cable 142, a first sleeve 160, a first lock pin 168, and a first compression spring 164. The first lock pin 168 and a first end effector 181 on the distal end of the first frame 176 form the first holder 173. The first lock pin 168 slides longitudinally in and out of a first lock pin hole 188 in the first end effector 181. The first cable 142 is fixedly attached to the first lock pin 168 by crimping, brazing, or other conventional techniques. The first cable 142 inserts slideably into a first channel 186 of the first frame 176, and is guided by the first sleeve 160. The first compression spring 164 is captured on the first cable 142 and between the first sleeve 160 and the first lock pin 168. The first compression spring 164 is always compressed so as to exert a force on the first lock 168 pin in the distal direction, thus biasing the first lock pin 168 to occupy the first lock pin hole 188 of the first frame 176. Retraction of the first lock pin 168 from the first lock pin hole 188 is accomplished by pulling on the first cable 142 in the proximal direction, as will be described later. The distal end of the first lock pin 168 is beveled so as to wedge against the needle 2 as it is trapped in a first groove 180 between the distal end of the first frame 176 and the first end effector 181. The first frame 176 is fixedly attached to the shaft tube 151 (see FIG. 2) by any one of numerous methods including spot welding or use of an adhesive.

The movable arm 174 comprises a second frame 178, a second cable 144, a second sleeve 162, a second compression spring 166, and a second lock pin 170. The second lock pin 170 and a second end effector 183 attached to the distal end of the second frame 178 form the second holder 175. The second lock pin 170 slides distally into a lock pin hole 200 of the second end effector 183 to hold the needle 2. The needle 2 is held transverse to the longitudinal axis of the second holder 175 in a groove 198 between the second end effector 183 and the distal end of the second frame 178. The second lock pin 170 holds the needle 2 against the second end effector 183. The needle 2 is released from the second holder 175 by pulling the second cable 144 in the proximal direction, thus releasing the force on the second lock pin 170 from the second compression spring 166.

The movable arm 174 is pivotably attached to the stationary arm 172 by a hinge pin 190 which rotatably inserts into first pivot hole 182 of the first frame 176, and fixedly inserts into a fourth pivot hole 194 of second frame 178. The distal end of a drive shaft 112 (see FIG. 2) rotatably inserts through a second pivot hole 184 of first frame 176 and fixedly inserts into a third pivot hole 192 of second frame 178. The longitudinal axis of the drive shaft 112 is coaxial with the longitudinal axis of the hinge pin 190, so that rotation of the drive shaft 112 causes the movable arm 174 to swing about its longitudinal axis. A sleeve 156 securely holds the stationary frame 176 in the shaft tube 151. Sleeve 156 is preferably made of stainless steel and presses tightly between the stationary frame 176 and the shaft tube 151. It is possible to eliminate the sleeve 156 by spot welding the first frame 176 to the shaft tube 151.

The lock pins, 170 and 168, the compression springs, 164 and 166, the flange sleeves, 160 and 162, and the holder frames, 176 and 178, are preferably made from metal such as stainless steel. The cables, 142 and 144, are preferably made of a braided stainless steel wire or from a liquid crystal polymer cord material. The sleeve 156 is preferably made from a metal such as stainless steel or from a medical grade polymer, such as UHMW polyethylene.

The design of the first and second holders, 173 and 175 respectively, allow for needles of various curvatures to be used with the present invention. The grooves, 180 and 198, are relatively wide compared to the needle 2. Also, the needle 2 is insertable into each of the grooves, 180 and 198, from a wide, angular range within the plane of motion of the needle 2. It is not necessary for the needle 2 to be exactly semi-circular, or for the approximate center of needle curvature to coincide exactly with the center of rotation of the needle 2 as it is held in the movable arm 174 and moves between the first and second positions about the longitudinal axis of the hinge pin 179 (see FIGS. 17 and 18). Therefore, the surgeon may use a plurality of sizes and shapes of needles.

Figure 19:
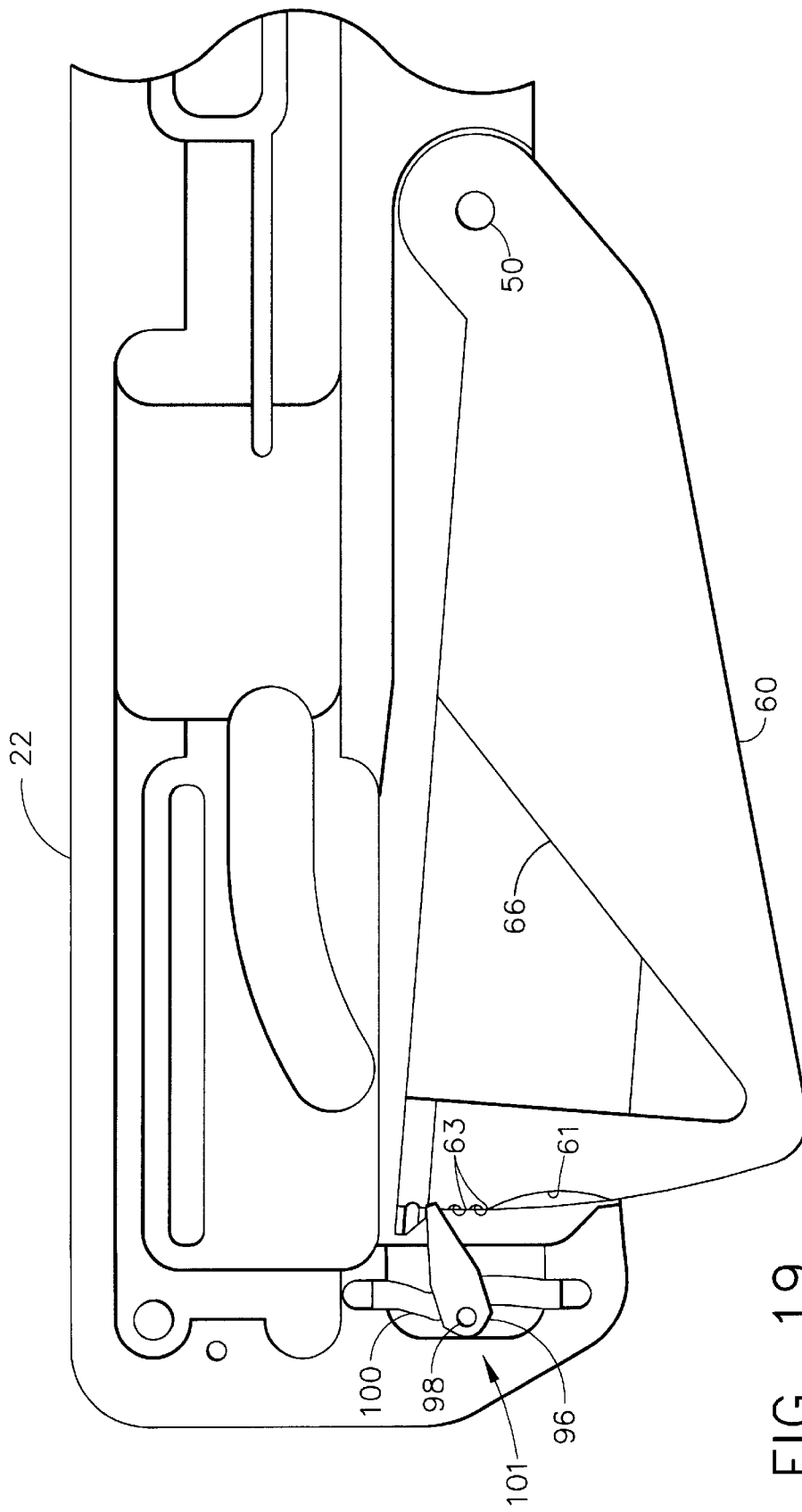
FIG. 19 is a side view of only some of the internal components of the handle, showing the interaction of a pawl with an actuator.

Turning again to FIG. 2, the components of the handle 20 are next described. The handle 20 comprises a left handle half 22 and a right handle half 24 which are attached together by fasteners (not shown) in fastener holes 32, 34, and 36. The handle halves, 22 and 24, are made of a rigid, medical grade polymer and together form an irregularly shaped inner cavity 42 for the operational support of the internal elements. Left and right actuator halves, 58 and 56, are pivotally attached to the handle halves, 22 and 24, by an actuator pin 50 inserted through holes 48, 62, and 64, thus forming the actuator 60. A proximal surface 65 of the actuator 60 is provided with a plurality of transverse grooves 63 that cooperate with an anti-backup pawl 96 (see FIG. 19). The distal end of the pawl 96 is pivotally mounted on a transverse pawl pin 98 which inserts into pawl hole 30 of the handle halves, 22 and 24. In near perpendicular conjunction therewith, a vertically disposed spring wire 100 passes through a clearance hole in the pawl 96, thus providing the pawl with a bilateral bias. As the distal end of the pawl 96 is deflected either upward or downward, the vertical spring wire 100 brings the pawl back to its center position. As the actuator 60 reaches full stroke (see FIG. 12), the distal end of the pawl 96 moves into an arcuate cutout 61 in the proximal surface 65 of the actuator 60, permitting the pawl to go to a center position. The actuator may then be released, returning to the position shown in FIG. 4. In this embodiment, the actuator 60 pivots about ten degrees about actuator pin 50 before being permitted to return to its start position. In like manner, as the actuator 60 is released, the pawl 96 prevents recompression of the actuator. A continuous stitch cycle is thereby provided which in effect prevents partial cycles and dropping of the needle. The pawl 36, pawl pin 98, pawl spring wire 100, and transverse grooves 63 are components of what is also referred to as a cycling device 101, which is shown in FIGS. 4 and 19.

Figure 12:
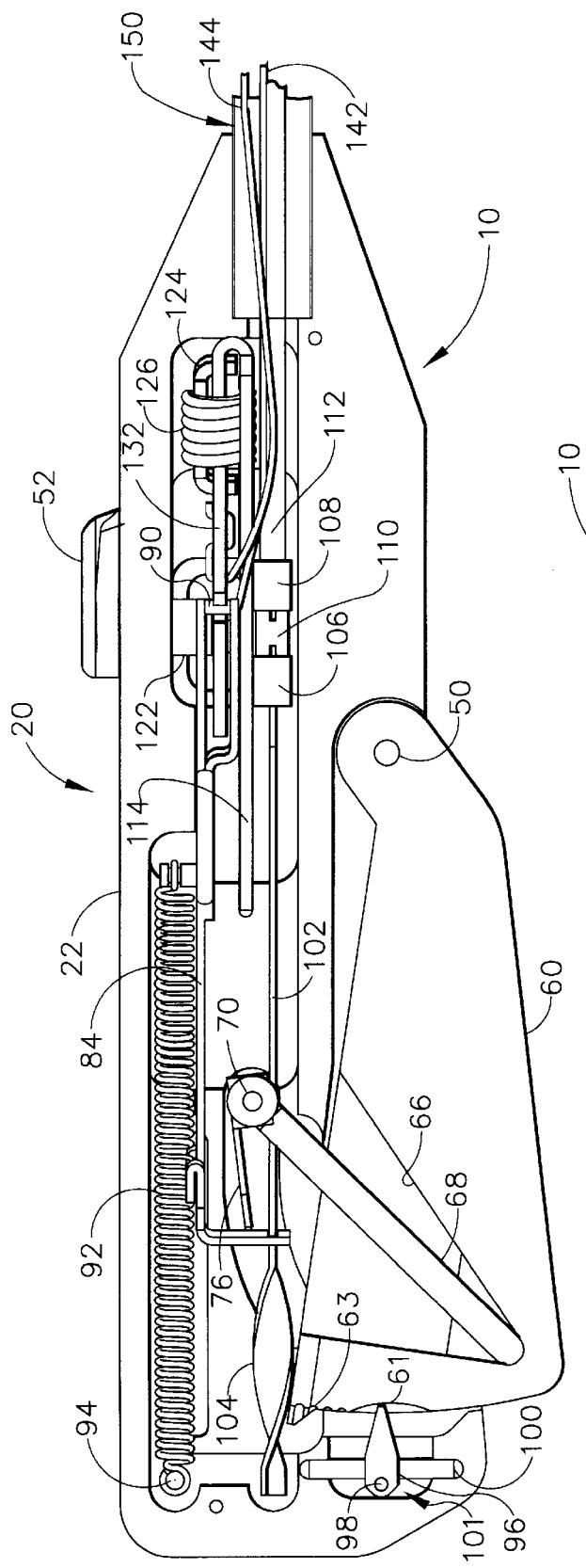
FIG. 12 is a side view of the internal components of the handle of the surgical device, for when the handle is in a third configuration.
Figure 13:
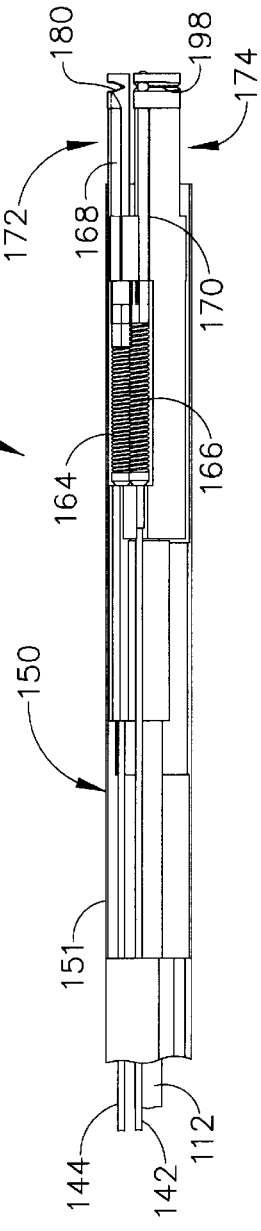
FIG. 13 is a side view of the internal components of the distal portion of the shaft of the surgical device, correlating with the third handle configuration of FIG. 12.
Figure 16:
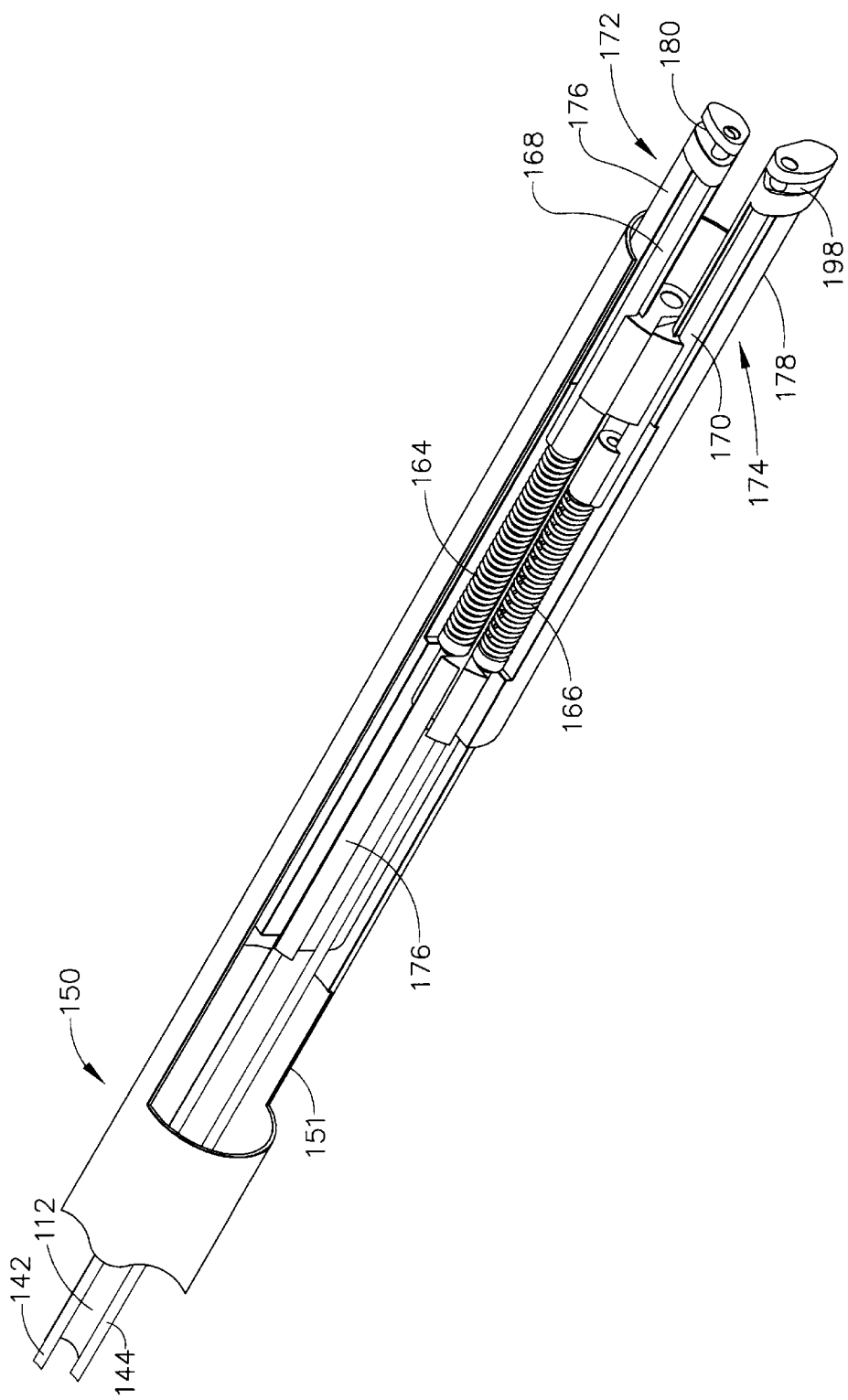
FIG. 16 is an isometric view of the distal portion of the surgical device, with a portion of the shaft tube cutaway for clarity, correlating with the third handle configuration of FIG. 12.

The actuator 60 is provided with a cavity 66 which cooperates with a connector rod 68 (FIG. 12). The bottom extremity of the connector rod 68 resides and pivots at the bottom of the cavity 66. The upper extremity has a left and a right roller, 74 and 72 respectively, which are guided in two arcuate slots, 26 and 27 (27 is hidden) provided in the handle halves, 22 and 24. The upper extremity of the connector rod 68 is pivotally attached to the distal end of a pull link 76 and reciprocates in a generally longitudinal path. The proximal end of the pull link 76 resides in a slot 83 (not visible in FIG. 2) at the lower proximal end of a slide bar 84. A second slot 82 is provided in the proximal end of the slide bar 84 below and in parallel relationship to the pull link slot 83. The second slot 82 of the slide bar 84 communicates with a flat shaft 102 having a helical proximal end 104. The distal end of the flat shaft 102 is fixedly attached to the drive shaft 112 by way of a coupling 110 and two connectors, 106 and 108. The distal end of the drive shaft 112, as was described previously, is attached to the movable arm 174 on the distal end of the surgical device 10. Thus, compression of the actuator causes rotation of the movable arm 174 from the second position (see FIG. 11) to the first position (see FIG. 17). Release of the actuator 60 allows the movable arm 174 to return again to the second position.

The slide bar 84 is provided with a pair of vertically disposed push pins 90 at its distal end, a centrally disposed spring post 88, and a pair of slide shoes 86 at its proximal end. The distal end of an extension spring 92 is attached to the spring post while its proximal end is pivotally attached to the handle halves, 22 and 24, by a pin 94 inserted into a hole 28. The extension spring 92 is enclosed in a longitudinal slot 24 in the inner cavity 42 of the handle 20. As the slide bar 84 is moved distally by the pull link 76, the spring 92 extends beyond the confines of the longitudinal slot 24 providing the distal end of the slide bar 84 a degree of lateral freedom. The slide bar 84 pivots to the right or to the left as it contacts a toggle plate 132 that is centrally located within the handle 20. At full extension of the spring 92, the distal portion thereof will be beyond the longitudinal slot of the inner cavity 42. As shown in FIG. 14, only the distal end of the spring 92 can deflect laterally. It is this foreshortened length that requires the slide bar 84 to return to the middle of the surgical device since only the distal end of the spring 92 is allowed to produce a side load at the distal end of the slide bar 84.

As the slide bar 84 moves distally, the flat shaft 102 rotates by virtue of its helical end 104, as described earlier. Full rotation is accomplished before the slide bar 84 comes into complete contact with the toggle plate 132. This operational sequence allows a dwell time between when the movable arm 174 moves from its second position (see FIG. 18) to its first position (see FIG. 17) and when the movable arm 174 releases the needle 2 and the stationary arm 172 holds the needle.

The toggle plate 132 (see FIGS. 9, 20, 21, 22) has a right cam surface 130 and a left cam surface 131 on its proximal end, forming a triangularly shaped extension. The toggle plate further includes, a toggle arm 128 on the distal end, a left wing 136 and a right wing 134. The left wing 136 has a left tab 137, while the right wing has a tab 135. The toggle plate pivots about toggle shaft 122, which is mounted to a stationary support plate 114, affixed between the handle halves, 22 and 24. Toggle shaft 122 extends outside of the handle halves through left and right recesses, 44 and 46 respectively, of the left and right handle halves, 22 and 24 respectively. A control 52 is attached to the upper end of the toggle shaft 122 so that the toggle plate 132 can be manually switched back and forth. The control 52 also provides visual feedback to the surgeon as to the sequence of operation of the device. The toggle arm 128 of the toggle plate 132 cooperates compressively against a toggle spring 126 that throws the toggle plate to the right or left. It will not remain in the center position. The toggle spring is retained about a toggle link 124 to a toggle tab 116 of the support plate 114. Opening 118 of the support plate 114 provides clearance for the toggle spring 126 to move back and forth laterally. The length of the toggle link 124 is set according to the lateral motion desired for the toggle plate 132. A longer length would result in greater lateral motion of the toggle plate 132 which in turn controls the distance the first and second cables, 142 and 144 respectively, are pulled. The first and second cables, 142 and 144, are adjustably attached during assembly to the left and right wings, 136 and 134 respectively, by being passed through a plurality of holes 140 in an "over and under" fashion. As already described for FIG. 3, pulling of first cable 142 results in the release of the needle 2 from the first holder 173 while pulling of second cable 144 results in the release of the needle 2 from the second holder 175.

Figure 20:
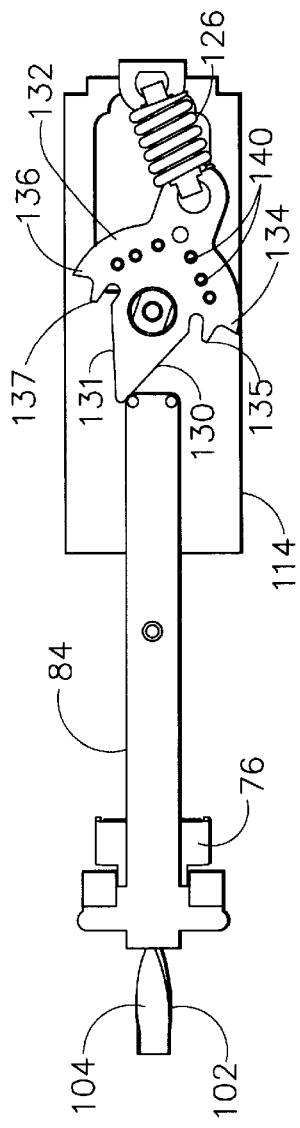
FIG. 20 is a top view of only some of the internal components of the handle, showing the interaction of a slide bar with a toggle plate which is in a first position.
Figure 21:
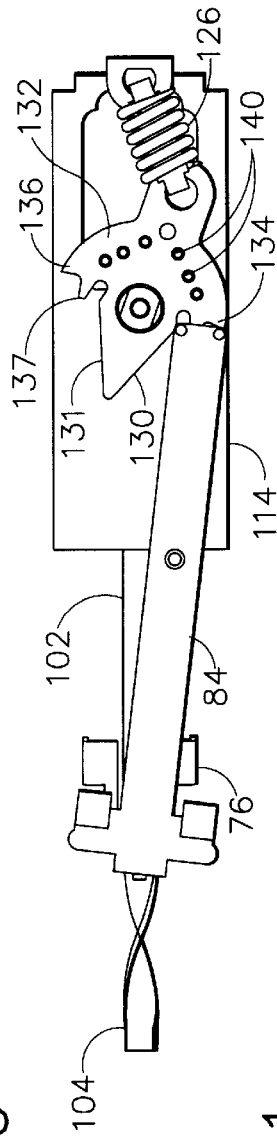
FIG. 21 is the same view as FIG. 20, but for when the slide bar has advanced distally (to the right)
Figure 22:
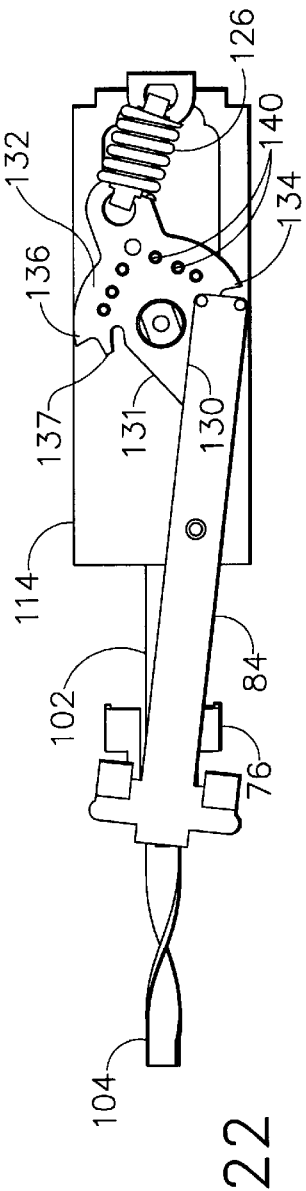
FIG. 22 is the same view as FIGS. 20 and 21, but for when the slide bar has advanced further distally, and showing the toggle plate flipped to a second position.

The interaction of the slide bar 84 with the toggle plate 132 is shown in sequences in FIGS. 20, 21, and 22. In FIG. 20, the push pins 90 of slide bar 84 have come into contact with right cam surface 130 of toggle plate 132, which is initially flipped to the right position. The distal advancement of the slide bar 84 causes the push pins 90 to engage with the right wing 134, so that the tab 135 (hidden) is interposed between the push pins like a chain belt on a bicycle sprocket see FIG. 21). The further distal advancement of the slide bar 84 causes the toggle plate 132 to flip to the left position as shown in FIG. 22, thus causing the pulling action on the first and second cables, 142 and 144, to reverse. If the slide bar 84 were to be retracted and then advanced distally again, it would first contact the left cam surface 131, then the left wing 136, and eventually cause the toggle plate 132 to flip again to the right position. When the slide bar 84 retracts, the flat shaft 102 rotates in the opposite direction as before, causing the movable arm 174 to move from its first position to its second position. The extension spring 92 pulls the slide bar 84, the pull link 76, and the actuator 60 back to the start position shown in FIG. 4.

The steps for using the present invention are next described for a typical surgical procedure requiring the placement of a plurality of stitches into soft tissue such as for joining together two blood vessels in a vascular anastomosis. For all the steps except loading of the needle 2 into the distal end, the device is operated with one hand.

The surgical device 10 normally is in the configuration shown in FIGS. 4–8. The actuator 60 is released so that the movable arm 174 is in the second position (see FIG. 8). The control 52 is pointed to the right so that the toggle plate 132 is also pointed to the right, and the lock pin 168 of the stationary arm 172 is extended distally into the first groove 180, while the lock pin 170 of the movable arm 174 is retracted from the second groove 198.

In FIGS. 9–10 the device is shown in the needle-loading configuration. The control 52 and the toggle plate 132 have been manually flipped to the left position, thus retracting the first lock pin 168 from the first groove 180 of the stationary arm 172. The blunt end 3 of the needle 2 is manually loaded into the first holder 173 with the sharp end 1 oriented as shown in FIG. 11. The control 52 is flipped back to the right position to cause the first holder 173 to clamp onto the needle 2. The movable arm 174 is still in the second position, which is removed from the stationary arm 172. The sharp end 1 of the needle 2 can now be placed into the tissue. The surgeon may rotate the device in a clockwise direction to gather tissue and completely penetrate through the tissue with the needle 2.

FIGS. 12–17 show the surgical device for when the actuator has been compressed, causing the movable arm 174 to rotate into position to clamp onto the sharp end 1 of the needle 2. Nearly simultaneously the stationary arm 172 releases the blunt end 3 of the needle 2.

The surgeon next releases the actuator 60 so that the movable arm 174 pulls the needle 2 with trailing suture filament 4 through the tissue, as shown in FIG. 18. The surgeon may then slowly withdraw the device from the surgical site, pulling suture filament through the tissue.

The actuator 60 of the device may be compressed again to reload the needle 2 into the first holder 173 so that another stitch may be place into tissue. Or the control 52 may be flipped to the right position to release the needle 2 from the second holder 175, and the above steps may be repeated using a new needle and suture filament.

What is claimed is:

1. A surgical device to assist in suturing body tissue, said surgical device comprising:
  a. a handle;
  b. an elongated shaft having a proximal end attached to said handle, a distal end, and a longitudinal axis extending therebetween;
  c. a stationary arm having a first holder for alternately holding and releasing a needle, said stationary arm attached to and extending from said distal end of said shaft, said stationary arm attached to said shaft such that its position, relative to said shaft, is fixed;
  d. a movable arm having a second holder, said second holder for alternately holding and releasing a needle, said movable arm extending from said distal end of said shaft, whereby said movable arm is rotatable about said longitudinal axis of said shaft; and
  e. an actuator for moving said second holder adjacent to said first holder and for passing a needle from one of said first and second holders to the other of said first and second holders.

2. The surgical device of claim 1, wherein said movable arm is rotatable by operation of said actuator between a first position and a second position,
  wherein for said first position, said second holder is adjacent to said first holder and
  wherein for said second position, said second holder is spaced further apart from said first holder.

3. The surgical device of claim 2, wherein said actuator includes a cycling device for preventing said second holder from reversing its rotational direction while rotating between said first position and said second position.

4. The surgical device of claim 1, wherein said actuator is operated by applying manual force.

5. The surgical device of claim 1, wherein said device further comprises a control on said handle for manually inserting and releasing said needle from at least one of said first and second holders.

6. The surgical device of claim 1, wherein said first holder comprises a first lock pin longitudinally movable within said stationary arm, and a first end effector attached to and distal to the distal end of said stationary arm, whereby said first lock pin moves distally to engage a needle against said first end effector, and moves proximally to release said needle from said end effector.

7. The surgical device of claim 1, wherein said second holder comprises a second lock pin longitudinally movable within said movable arm, and a second end effector attached to and distal to the distal end of said movable arm, whereby said second lock pin moves distally to engage a needle against said second end effector, and moves proximally to release said needle from said second end effector.

8. The surgical device of claim 1 further comprising an arcuate needle having a radius commensurate with the rotational radius of said second holder, wherein each of said first and second holders hold said needle such that the curvature of said needle is oriented around said longitudinal axis of said shaft.

9. A method of using the surgical device of claim 1 comprising:
  a. holding a proximal portion of a needle having a suture filament attached thereto in said first holder of said stationary arm;
  b. placing a distal portion of said needle through said tissue;
  c. actuating said actuator so as to move said second holder adjacent to said first holder and releasing said proximal portion of said needle from said first holder and holding said distal portion of said needle in said second holder;
  d. releasing said actuator and rotating said second holder around said axis of said shaft away from said first holder, and passing said distal portion of said needle and a portion of said suture filament attached thereto, through said tissue.

10. The method of claim 9 further comprising two additional steps after step (d):
   a. actuating said actuator and rotating said second holder adjacent to said first holder, and releasing said distal portion of said needle from said second holder and holding said proximal portion of said needle in said first holder, and
   b. releasing said actuator and rotating said second holder away from said first holder while said proximal portion of said needle remains held by said first holder.

11. A surgical device to assist in suturing body tissue, said surgical device comprising:
   a. a handle;
   b. an elongated shaft having a proximal end attached to said handle, a distal end, and a longitudinal axis extending therebetween;
   c. a stationary arm having a first holding means for alternately holding and releasing a needle, said stationary arm attached to and extending from said distal end of said shaft, said stationary arm attached to said shaft such that its position, relative to said shaft, is fixed;
   d. a movable arm having a second holding means, said second holding means for alternately holding and releasing a needle, said movable arm extending from said distal end of said shaft, whereby said movable arm is rotatable about said longitudinal axis of said shaft;
   e. an actuating means for moving said second holder adjacent to said first holder and for passing a needle from one of said first and second holding means to the other of said first and second holding means.

12. The surgical device of claim 11, wherein said movable arm is rotatable by operation of said actuator between a first position and a second position;
   wherein for said first position, said second holding means is adjacent to said first holding means;
   wherein for said second position, said second holding means is spaced further apart from said first holding means.

13. The surgical device of claim 11, wherein said actuating means includes a cycling device for preventing said second holding means from reversing its rotational direction while rotating between said first position and said second position for each complete actuation of said actuating means.

14. The surgical device of claim 11, wherein said actuating means is operated by applying manual force.

15. The surgical device of claim 11, wherein said device further comprises a control on said handle for opening and closing said first and second holding means.

16. The surgical device of claim 11, wherein said first holding means comprises a first lock pin longitudinally movable within said stationary arm, and a first end effector attached to and distal to the distal end of said stationary arm, whereby said first lock pin moves distally to engage a needle against said first end effector, and moves proximally to release said needle from said end effector.

17. The surgical device of claim 11, wherein said second holding means comprises a second lock pin longitudinally movable within said movable arm, and a second end effector attached to and distal to the distal end of said movable arm, whereby said second lock pin moves distally to engage a needle against said second end effector, and moves proximally to release said needle from said second end effector.

18. The surgical device of claim 11 further comprising an arcuate needle having a radius commensurate with the rotational radius of said second holding means, wherein each of said first and second holding means hold said arcuate needle such that the curvature of said needle is oriented around said longitudinal axis of said shaft.

19. A method for suturing tissue, said method comprising:
   a. providing a device comprising a handle for holding said device, said handle having distal and proximal ends and first and second arms extending distally from said handle, said arms having proximal ends attached to said handle and distal ends having holders attached thereto for holding and releasing a needle, said first arm being stationary such that its position, relative to said handle is fixed, said second arm being movable such that it is rotatable about a longitudinal axis of said handle, and at least one actuator for moving said second arm such that said distal end of said arms are closely adjacent to one another and for passing said needle from one holder to the other and thereafter for moving said distal ends of said arms further apart from one another by rotating said second arm, said first holder holding a needle having a suture attached thereto;
   b. manually placing a distal end of said needle through said tissue;
   c. rotating said second arm by actuating said at least one mechanism so as to move said arms closely adjacent one another so that said second holder holds said needle, releasing said needle from said first holder, and rotating said second arm and thereby moving said distal ends of said arms further apart from one another; and
   d. removing said needle from said tissue.

* * * * *